United States Patent [19]

Nestler

[11] Patent Number: 5,994,289

[45] Date of Patent: *Nov. 30, 1999

[54] SURFACTANT MIXTURES COMPRISING ACYLOXYALKANESULFONATES

[75] Inventor: Bernd Nestler, Frankfurt, Germany

[73] Assignee: Clariant GmbH, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/936,389

[22] Filed: Sep. 25, 1997

[30] Foreign Application Priority Data

Oct. 1, 1996 [DE] Germany ................... 196 40 573

[51] Int. Cl.$^6$ ................... C11D 1/12; C11D 1/28
[52] U.S. Cl. ................... 510/495; 510/153; 510/426; 510/437; 554/90; 554/156; 554/92
[58] Field of Search ................... 554/88, 90, 92, 554/97, 154, 155, 156, 158; 510/152, 137, 403, 237, 151, 484, 141, 138, 153, 426, 437, 495

[56] References Cited

U.S. PATENT DOCUMENTS

| | | | |
|---|---|---|---|
| 3,029,264 | 4/1962 | Alphen et al. | 260/400 |
| 4,536,338 | 8/1985 | Urban et al. | 260/400 |
| 5,041,233 | 8/1991 | Kutney et al. | 252/121 |
| 5,384,421 | 1/1995 | Day et al. | 554/92 |
| 5,473,089 | 12/1995 | Gutsche et al. | 554/92 |
| 5,646,320 | 7/1997 | Cassady et al. | 554/149 |
| 5,777,140 | 7/1998 | Buhring | 554/92 |

FOREIGN PATENT DOCUMENTS

| | | | |
|---|---|---|---|
| 0073626 | 3/1983 | European Pat. Off. | C07C 143/10 |
| A-0585071 | 3/1994 | European Pat. Off. | |
| WO 94/09107 | 4/1994 | WIPO . | |

Primary Examiner—Yogendra Gupta
Assistant Examiner—Gregory E. Webb
Attorney, Agent, or Firm—Miles B. Dearth

[57] ABSTRACT

Surfactant mixtures containing acyloxyalkanesulfonates, which are prepared by mixing different acyloxyalkanesulfonates, the total quantity of acyloxyalkanesulfonates comprising a mixture of ammonium and alkali metal and/or alkaline-earth metal cations.

11 Claims, No Drawings

SURFACTANT MIXTURES COMPRISING ACYLOXYALKANESULFONATES

This application claims priority from Federal Republic of Germany Application 19640573.4 filed Oct. 1, 1996.

BACKGROUND OF THE INVENTION

Acyloxyalkanesulfonates are anionic surfactants which are used as starting material for syndet soaps, cosmetics and cleaning formulations. They are notable for good foaming properties, good hard water stability and good skin compatibility.

A disadvantage of using these surfactants is the fact that most of them are brittle solids which melt or are stirrable only at high temperatures. At these high temperatures, which are necessary in order to render the acyloxyalkanesulfonate at all processable, the latter is very sensitive to oxidation, thermal decomposition begins and discolorations appear.

Accordingly, it is advantageous to lower the melting point or the temperature at which acyloxyalkanesulfonates are stirrable and thus processable. To solve this problem, it is already known to prepare acyloxyalkanesulfonates which are mixed salts, in which the cation is a mixture of two different cations, for example sodium and potassium ions (U.S. Pat. No. 3,029,264). These acyloxyalkanesulfonates, preferably acyl-isethionates, are prepared by esterification of fatty acids using mixtures of salts of isethionic acid, these salts having different cations. In this way, the formation of discolorations is avoided.

SUMMARY OF THE INVENTION

Acyloxyalkanesulfonates with mixed cations are also described in WO 94/09107. The cations which are suitable there are exclusively magnesium, potassium and sodium.

The invention provides surfactant mixtures containing acyloxyalkanesulfonates, prepared by reaction of one or more fatty acids with at least one ammonium, alkali metal and/or alkaline-earth metal hydroxyalkanesulfonate to form a first acyloxyalkanesulfonate, where before, during or after the preparation of this first acyloxyalkanesulfonate, at least one second ammonium, alkali metal and/or alkaline-earth metal acyloxyalkanesulfonate is added, the cations in the hydroxyalkanesulfonate and in the second acyloxyalkanesulfonate being chosen such that the total quantity of acyloxyalkanesulfonate in the surfactant mixture is in the form of a mixed ammonium and alkali metal and/or alkaline-earth metal salt.

DESCRIPTION OF THE PREFERRED EMBODIMENTS

Preference is given to surfactant mixtures according to the invention which are prepared such that the acyloxyalkanesulfonates present therein have the following molar ratios of cations:

K:$NH_4$ from 97:3 to 9:95; Na:$NH_4$ from 98:2 to 5:95, in particular 97:3 to 50:50; Na:$NH(C_2H_5)_3$ from 98:2 to 10:90; K:$NH(C_2H_5)_3$ from 98:2 to 10:90.

Suitable fatty acids include saturated or unsaturated fatty acids containing 8 to 32 carbon atoms. Examples which may be given are caproic acid, capric acid, lauric acid, myristic acid, stearic acid, arachidic acid, oleic acid, linoleic acid and linolenic acid. Mixtures of fatty acids, such as, for example, coconut fatty acid and tallow fatty acid, are preferred. As well as unbranched fatty acids, branched fatty acids are suitable, for example 2-ethylhexanoic acid, 2-pentyloctanoic acid, 2-butylnonanoic acid, 2-propyldecanoic acid, 2-ethylundecanoic acid, 2-butylundecanoic acid, 2-methyldodecanoic acid, 2-ethyltridecanoic acid and 2-methyltetradecanoic acid and mixtures thereof.

The hydroxyalkanesulfonates conform to the formula HO-$R^1$-$SO_3$X, where $R^1$ is —$CH_2CH_2$—, —$(CH_2)_3$—, —$CH_2CH(CH_3)$— or —$CH_2CH_2OCH_2CH_2$—, ethylene being preferred.

Here, X is either an ammonium ion, preferably an ammonium ion of the formula $R^1$, $R^2$, $R^3$, $R^4N^{\oplus}$, where $R^1$, $R^2$, $R^3$ and $R^4$ can be identical or different, and are hydrogen, $C_1$–$C_4$-alkyl or $C_1$–$C_4$-hydroxyalkyl, or an alkali metal and/or alkaline-earth metal cation. Preference is given to sodium; potassium; $\oplus NH(CH_3)_3$; $\oplus NH(C_2H_5)_3$; $\oplus NH(CH_2CH_2OH)_3$ and $\oplus NH_4$; X can also be a mixture of different ammonium ions.

The reaction of the fatty acid with the hydroxyalkanesulfonate takes place by processes known per se, preferably by the process of direct esterification by reacting an excess of fatty acid with the hydroxyalkanesulfonate in the presence of an esterification catalyst at a temperature of from 100 to 260° C. with the simultaneous removal of water. The details of this direct esterification are as given in EP-A-0 585 071 (U.S. Pat. No. 5,384,421), which is incorporated herein by reference.

The hydroxyalkanesulfonic acid salts can be used as they are, preferably being used in the form of an aqueous solution, in general as a 40 to 65% by weight solution.

Suitable esterification catalysts are described in detail in the cited EP-A-0 585 071. They are alkanesulfonic acids, hydroxyalkanesulfonic acids, arylsulfonic acids, inorganic acids such as sulfuric acid, phosphoric acid, phosphorous acid, boric acid or their anhydrides, heavy-metal salts such as zinc sulfate, zirconium sulfate, zinc isethionate, zinc borate, aluminum sulfate, titanium sulfate or tungsten phosphate, metal oxides such as zinc oxide, aluminum oxide, magnesium oxide, cerium oxide, zirconium oxide or lanthanum oxide, and also mixtures of two or more of said catalysts and soaps which are formed from heavy metals and metal oxides. A particularly preferred esterification catalyst is zinc oxide. The esterification catalyst is used in a quantity of in general from 0.05 to 2% by weight, preferably 0.05 to 1% by weight, based on hydroxyalkanesulfonate.

In detail, the esterification can be carried out by introducing the fatty acid, the hydroxyalkanesulfonate(s) and the esterification catalyst into a reaction vessel at atmospheric pressure, and heating the mixture to the aforementioned temperature while stirring. The water which may have been introduced into the reaction mixture with the starting components and the water formed in the esterification reaction is continually discharged from the reaction mixture. Furthermore, it can also be advantageous to distill off some of the excess fatty acid during or after the esterification reaction.

The esterification reaction can also be carried out initially at atmospheric pressure and then by applying a vacuum to discharge the water more quickly. The time required to give the desired conversion of fatty acid and hydroxyalkanesulfonate is about 4 to 8 hours. A 100% conversion is not usually aimed at, for example because of time reasons, but instead the esterification reaction is interrupted, for example by cooling, at a lower percentage, for example at 75 to 90% by weight of acyloxyalkanesulfonate. The resultant reaction product is liquid or solid at room temperature.

In order to lower the viscosity of the reaction mixture, consistency regulators can in all cases be added to the reaction mixture before or during the cooling process. Suitable consistency regulators are, for example, paraffins, as described in EP-A-0 585 071, fatty acids, fatty acid esters of low molecular weight alcohols, or polyethylene glycols, or mixtures of consistency regulators. Preference is given to free fatty acids, particularly those which have a different chain length to the fatty acid used for the preparation of the acyloxyalkanesulfonate. The proportion of these consistency regulators can be up to 60% by weight, preferably up to 30% by weight. Preference is given to mixtures with up to 30% by weight of paraffin, up to 50% by weight of fatty acid and up to 10% by weight of polyethylene glycol. The percentages refer in each case to the sum of all components.

It is of considerable importance for the surfactant mixtures according to the invention that the acyloxyalkanesulfonates contained therein comprise, in their totality, not one single cation, but a mixture of different cations, at least one of these cations being an ammonium cation as defined above and the residual proportion comprising alkali metal and/or alkaline-earth metal cations or other ammonium cations. This is achieved by admixing another acyloxyalkanesulfonate, which will be referred to here as the second acyloxyalkanesulfonate, before, during or after the preparation of the first acyloxyalkanesulfonate.

This second acyloxyalkanesulfonate can likewise be in the form of an ammonium salt, an alkali metal salt and/or an alkaline-earth metal salt or a salt with a mixture of these cations. The type of cation in this second acyloxyalkanesulfonate depends on the type of cation in the first acyloxyalkanesulfonate since the prepared surfactant mixture must contain both ammonium cations as well as alkali metal and/or alkaline-earth metal cations. This is achieved, for example, by preparing an alkali metal and/or alkaline-earth metal acyloxyalkanesulfonate as a first acyloxyalkanesulfonate, and admixing an ammonium acyloxyalkanesulfonate on its own or a mixture of ammonium acyloxyalkanesulfonate and alkali metal and/or alkaline-earth metal acyloxyalkanesulfonate as a second acyloxyalkanesulfonate. Conversely, an ammonium hydroxyalkanesulfonate can be used to prepare an ammonium acyloxyalkanesulfonate as a first acyloxyalkanesulfonate, and an alkali metal or alkaline-earth metal acyloxyalkanesulfonate on its own or a mixture of alkali metal and/or alkaline-earth metal acyloxyalkanesulfonate and ammonium acyloxyalkane-sulfonate can be admixed as a second acyloxyalkanesulfonate. It is also possible to prepare a mixture of ammonium acyloxyalkanesulfonate and alkali metal and/or alkaline-earth metal acyloxyalkanesulfonate as a first acyloxyalkanesulfonate, and introduce, as a second acyloxyalkanesulfonate, an ammonium, alkali metal and/or alkaline-earth metal acyloxyalkanesulfonate or a mixture of ammonium and alkali metal and/or alkaline-earth metal acyloxyalkanesulfonate into the surfactant mixture according to the invention. Those surfactant mixtures which contain three or more different types of cation, at least one of which must be an ammonium cation, are also in accordance with the invention. Examples of these are acyloxyalkanesulfonates with a mixture of sodium, potassium and $NH_4^\oplus$ ions.

The prepared, second acyloxyalkanesulfonate is prepared separately, for example by the acid chloride process or by the already mentioned process of direct condensation from the same starting materials as described above. Because of an excess of fatty acid in the condensation and incomplete conversion, such an acyloxyalkanesulfonate still contains, to a greater or lesser extent, residual amounts of free fatty acids.

The second acyloxyalkanesulfonate is added before, during or after the preparation of the first acyloxyalkanesulfonate. Preferably, an acyloxyalkanesulfonate is prepared first and the second acyloxyalkanesulfonate, either in solid or in liquid form, is added to the still hot reaction mixture using suitable devices, for example in a stirred vessel or using a mixing, stirring, homogenizing or cavity transfer device, for example in a Cavitron device. It is also possible to carry out the mixing separately from the preparation process for the first acyloxyalkanesulfonate, by melting one or more prepared acyloxyalkanesulfonates, adding the second acyloxyalkanesulfonate(s) in liquid or solid form to the melt and then homogenizing the mixture.

The surfactant mixtures prepared in the manner described, which contain as main component acyloxyalkanesulfonates with mixed cations and in addition residual quantities of free fatty acids and optionally consistency regulators, are characterized, compared with similar products of the prior art (U.S. Pat. No. 3,029,264), by the fact that the temperature limit at which the surfactant mixture is still stirrable is markedly lower for the same content of acyloxyalkanesulfonate. This lowering of the stirrability limit for the surfactant mixtures according to the invention means that the content of acyloxyalkanesulfonate can be higher here than in the said prior art mixtures. The stirrability limit can be lowered further by adding consistency regulators. Furthermore, the residual content of free isethionate in the surfactant mixtures according to the invention is markedly lower.

EXAMPLE 1

236 g of coconut fatty acid, 255 g of aqueous sodium isethionate solution (58%) and 0.71 g of zinc oxide were introduced into a 2 l flask with ground glass joints fitted with stirrer, descending distillation bridge, internal thermometer and nitrogen line. The mixture was heated to 210° C. and the water formed in the direct condensation was distilled off. When the content of detergent-active substance was 78% (Epton's titration), 56 g of ammonium cocoylisethionate (84% strength product, which also contains coconut fatty acid) were added at a temperature of 178° C., and the mixture was stirred for 0.5 h at approximately 170° C. and then slowly cooled. The resultant sodium/ammonium cocoylisethionate mixture could still be stirred at a temperature of 105° C. and contained 82% of washing-active substance (Epton's titration) and 4.3% of free hydroxyethanesulfonate. If 14.2 g of stearic acid were also added, the mixture, having a WAS content of 74% and a hydroxyethanesulfonate content of 3.7%, could still be stirred at a temperature of 95° C.

The mixtures recited in the following examples were prepared by melting and mixing the corresponding acyloxyalkanesulfonates. Whilst cooling these mixtures, the sintering points and the onset of melting given in the respective tables were measured. The amount of acyloxyalkanesulfonate in these mixtures is more than 95% by weight.

| K salt [%] | $NH_4$ salt [%] | Sintering point [° C.] | Onset of melting [° C.] |
|---|---|---|---|
| Example 2 K/$NH_4$ lauroylisethionate | | | |
| 0 | 100 | 150 | 160 |
| 25 | 75 | 140 | 150 |
| 50 | 50 | 150 | 162 |
| 75 | 25 | 168 | 178 |
| 85 | 15 | 170 | 190 |
| 90 | 10 | 179 | 190 |

-continued

| K salt [%] | NH4 salt [%] | Sintering point [° C.] | Onset of melting [° C.] |
|---|---|---|---|
| 95 | 5 | 192 | 207 |
| 100 | 0 | 227 | 235 |

Example 3
Na/NH4 lauroylisethionate

| | | | |
|---|---|---|---|
| 0 | 100 | 150 | 160 |
| 25 | 75 | 150 | 162 |
| 30 | 70 | 152 | 165 |
| 50 | 50 | 157 | 173 |
| 75 | 25 | 161 | 181 |
| 85 | 15 | 185 | 195 |
| 90 | 10 | 195 | 202 |
| 95 | 5 | 198 | 210 |
| 100 | 0 | 220 | 230 |

Example 4
Na/NH(Et3) lauroylisethionate

| | | | |
|---|---|---|---|
| 0 | 100 | liquid | |
| 25 | 75 | still pourable | |
| 50 | 50 | pasty | |
| 75 | 25 | waxy | |
| 85 | 15 | 160 | 191 |
| 90 | 10 | 173 | 200 |
| 95 | 5 | 185 | 205 |
| 100 | 0 | 220 | 230 |

Example 5
K/NH(Et3) lauroylisethionate

| | | | |
|---|---|---|---|
| 0 | 100 | liquid | |
| 25 | 75 | still pourable | |
| 50 | 50 | pasty | |
| 75 | 25 | waxy | |
| 85 | 15 | 178 | 206 |
| 90 | 10 | 190 | 211 |
| 95 | 5 | 197 | 217 |
| 100 | 0 | 227 | 235 |

What is claimed is:

1. A surfactant mixture containing acyloxyalkanesulfonate, prepared by reaction of one or more fatty acids with at least one ammonium, alkali metal and/or alkaline-earth metal hydroxyalkanesulfonate to form a first acyloxyalkanesulofnate, where before, during or after the preparation of said first acyloxyalkanesulfonate, at least one second different ammonium, alkali metal and/or alkaline-earth metal acyloxyalkanesulfonate is added, the cations in said hydroxyalkanesulfonate and in said second acyloxyalkanesulfonate being chosen such that the total quantity of acyloxyalkanesulfonate in the surfactant mixture contains ammonium cation and alkali metal cation wherein said alkali metal cations are selected from the group consisting of sodium and potassium, including mixtures, and wherein the molar ratio of potassium to ammonium cation is from 97:3 to 9:95 and the molar ratio of sodium to ammonium cations is from 98:2 to 5:95, wherein the surfactant mixture contains an excess of unreacted fatty acids.

2. A surfactant mixture as claimed in claim 1, wherein the acyloxyalkanesulfonate is an acylisethionate.

3. A surfactant mixture as claimed in claim 1, wherein the ammonium cation of the hydroxyalkanesulfonate and of the acyloxyalkanesulfonate conforms to the formula $$R^1R^2R^3R^4N^{\oplus}$$

where $R^1$, $R^2$, $R^3$ and $R^4$ are hydrogen, $C_1$–$C_4$-alkyl or $C_1$–$C_4$-hydroxyalkyl.

4. A surfactant mixture as claimed in claim 1, prepared by reacting coconut fatty acid.

5. A process for preparing acyloxyalkanesulfonate product having a reduced sintering point temperature and temperature of onset of melting, comprising (1) reacting an excess of one or more fatty acids with at least one ammonium, alkali metal and/or alkaline-earth metal hydroxyalkanesulfonate to form a first acyloxyalkanesulfonate, wherein before, during or after step (1) at least one second ammonium, alkali metal and/or alkaline-earth metal salt of an acyloxyalkanesulfonate is added, said second cation differing from said cation of said first acyloxyalkanesulfonate, wherein the acyloxyalkanesulfonate product resulting therefrom is a surfactant mixture comprising ammonium cations together with alkali metal and/or alkaline earth metal cation(s), said product has a temperature limit at which said product is still stirrable that is lower than the corresponding acyloxyalkanesulfonate alkali and/or alkaline-earth salt.

6. The process of claim 5 wherein said second acyloxyalkanesulfonate is added before the reaction of step (1).

7. The process of claim 5 wherein said second acyloxyalkanesulfonate is added during the reaction of step (1).

8. The process of claim 5 wherein said second acyloxyalkanesulfonate is added after the reaction of step (1).

9. The process of claim 5 wherein the acyloxyalkanesulfonate is an acylisethionate.

10. The process of claim 5 wherein the ammonium cation of said hydroxyalkanesulfonate has the following formula:

$$R^1R^2R^3R^4N^{\oplus}$$

Where $R^1$, $R^2$, $R^3$, and $R^4$ are hydrogen, $C_1$–$C_4$-alkyl or $C_1$–$C_4$-hydroxyalkyl.

11. The process of claim 5 wherein wherein said product contains alkali metal cation(s) selected from the group consisting of sodium and potassium, including mixtures, and wherein the molar ratio of potassium to ammonium cation is from 97:3 to 9:95 and the molar ratio of sodium to ammonium cations is from 98:2 to 5:95.

* * * * *